(12) United States Patent
Cui et al.

(10) Patent No.: US 10,313,098 B2
(45) Date of Patent: Jun. 4, 2019

(54) CLOCK SYNCHRONIZING

(71) Applicant: Shenyang Neusoft Medical Systems Co., Ltd., Shenyang (CN)

(72) Inventors: Gai Cui, Shenyang (CN); Long Yang, Shenyang (CN); Jun Zhang, Shenyang (CN); Peng Ning, Shenyang (CN); Zhenguo Zhang, Shenyang (CN)

(73) Assignee: Shenyang Neusoft Medical Systems Co., Ltd., Shenyang (CN)

( * ) Notice: Subject to any disclaimer, the term of this patent is extended or adjusted under 35 U.S.C. 154(b) by 0 days.

(21) Appl. No.: 15/798,806

(22) Filed: Oct. 31, 2017

(65) Prior Publication Data

US 2018/0123773 A1    May 3, 2018

(30) Foreign Application Priority Data

Nov. 1, 2016    (CN) .......................... 2016 1 0942196

(51) Int. Cl.
*H04L 7/00*    (2006.01)
*A61B 6/00*    (2006.01)
(Continued)

(52) U.S. Cl.
CPC ............ *H04L 7/0012* (2013.01); *A61B 6/582* (2013.01); *G01T 1/2985* (2013.01);
(Continued)

(58) Field of Classification Search
CPC .................................................. H04L 7/0012
(Continued)

(56) References Cited

U.S. PATENT DOCUMENTS 9,989,928 B2 *    6/2018    Wu ...................... H03M 3/414
2003/0107417 A1    6/2003    Roberts
(Continued)

FOREIGN PATENT DOCUMENTS

CN    103383539 A    11/2013
CN    105262463 A    1/2016

OTHER PUBLICATIONS

State Intellectual Property Office of the People's Republic of China, Office Action and Search Report Issued in Chinese Application No. 201610235943.1 dated Oct. 20, 2017, 6 pages (with English-language translation thereof, 7 pages).

*Primary Examiner* — Lihong Yu
(74) *Attorney, Agent, or Firm* — Fish & Richardson P.C.

(57) ABSTRACT

Methods, systems, and machine-readable storage mediums for clock synchronizing among detectors in a clock synchronizing configuration are provided. An example clock synchronizing method includes: providing a clock of a preset frequency in each of N modules to be synchronized, coupling every two adjacent modules of the modules by a transmission line of the same length, N being an odd number, selecting two different modules from the modules as two reference modules respectively, controlling each of the reference modules to transmit a synchronizing signal to the other modules, determining a clock error between every two modules having the same transmission distance from the reference module according to a moment of the synchronizing signal reaching each of the other modules, selecting a calibrating module from the modules, and implementing clock synchronization between each of the modules and the calibrating module according to the respective clock errors associated with the two reference modules.

18 Claims, 7 Drawing Sheets

(51) Int. Cl.
*H04L 7/04* (2006.01)
*G01T 1/29* (2006.01)
*G04F 10/00* (2006.01)
*A61B 6/03* (2006.01)
*H04L 29/08* (2006.01)

(52) U.S. Cl.
CPC .......... *G04F 10/005* (2013.01); *H04L 7/0008* (2013.01); *H04L 7/0037* (2013.01); *H04L 7/04* (2013.01); *A61B 6/037* (2013.01); *H04L 67/12* (2013.01)

(58) Field of Classification Search
USPC ........................................................ 375/356
See application file for complete search history.

(56) References Cited

U.S. PATENT DOCUMENTS

| | | | | |
|---|---|---|---|---|
| 2004/0008720 | A1* | 1/2004 | Wang | H04L 12/422 370/460 |
| 2010/0085885 | A1* | 4/2010 | Sakurada | H04J 3/0667 370/252 |
| 2015/0200680 | A1* | 7/2015 | Xie | G01T 1/17 341/166 |

* cited by examiner

CLOCK SYNCHRONIZING

CROSS REFERENCE TO RELATED APPLICATIONS

This application claims priority to Chinese Patent Application No. 201610942196.5, filed on Nov. 1, 2016, the entire content of which is incorporated herein by reference.

TECHNICAL FIELD

The present disclosure relates to clock synchronizing.

BACKGROUND

In a Positron Emission Tomography (PET) system, a front-end detection part may include a crystal, a photoelectric sensor and a signal processing circuit. For example, a number of crystals, a photoelectric sensor and a signal processing circuit may be integrated into a detector, and a plurality of detectors may form the front-end detection part of the PET system. The PET system may include a plurality of detector rings in an axial direction. Each of the detectors in the detector ring may be closely arranged circumferentially. When the PET system is used to perform a disease diagnosis on a subject, a to-be-detected part of the subject may be placed in the detector rings. Thus, when a radionuclide injected into the subject's body emits a positron therein and the positron annihilates with a negatron in the subject's body to generate a pair of gamma-photons opposite in direction, the pair of gamma-photons may be collected and detected by detectors. Then, energy information of any one of the pair of photons and the moment of the photon reaching the corresponding detector can be calculated by a back-end electronic system of the PET system, and PET detection may be completed through subsequent calculation.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, Magnetic Resonance Imaging (MRI), digital X-ray machine, ultrasound, Positron Emission Tomography (PET), Linear Accelerator (LINAC), and biochemistry analyser. Currently, NMS' products are exported to over 60 countries and regions around the globe, serving more than 5,000 renowned customers. NMS's latest successful developments, such as 128 Multi-Slice CT Scanner System, Superconducting MRI, LINAC, and PET products, have led China to become a global high-end medical equipment producer. As an integrated supplier with extensive experience in large medical equipment, NMS has been committed to the study of avoiding secondary potential harm caused by excessive X-ray irradiation to the subject during the CT scanning process.

SUMMARY

The present disclosure provides methods, systems, and machine-readable storage mediums for clock synchronizing among detectors in a clock synchronizing configuration, which can effectively reduce design costs and structural complexity of the clock synchronizing configuration.

One aspect of the present disclosure features a clock synchronizing method including: coupling every two adjacent modules of a plurality of modules by a respective transmission line, the respective transmission lines having a same length, each module having a respective clock of a preset frequency to be synchronized, a number of the plurality of modules N being an odd number; selecting two different modules from the plurality of modules as two reference modules, respectively; for each of the reference modules, controlling the reference module to transmit a respective synchronizing signal simultaneously in a clockwise direction and an anticlockwise direction via the respective transmission lines until modules other than the reference module in the plurality of modules respectively receive the synchronizing signal once; determining, for every two modules of the other modules that have a same transmission distance from the reference module, a respective clock error between the two modules based on moments of the synchronizing signal reaching the two modules; selecting a calibrating module from the plurality of modules; and implementing clock synchronization between each of the plurality of modules and the calibrating module according to the determined respective clock errors for the two reference modules.

In some implementations, a clock synchronization configuration includes N−1 modules of the plurality of modules, and the method further includes: adding an additional module to the N−1 modules to obtain the N modules, the additional module being provided with a clock of the preset frequency to be synchronized.

In some implementations, determining the respective clock error between the two modules based on moments of the synchronizing signal reaching the two modules includes: for each of the two modules, measuring a respective time interval between an edge of a local clock cycle during which the synchronizing signal reaches the module and the moment of the synchronizing signal reaching the module; and determining the clock error between the two modules based on the measured respective time intervals.

Measuring the respective time interval can include: using at least one of a Time-to-Digital Converter (TDC) or a delay chain in Field-Programmable Gate Array (FPGA) in the module. In some cases, measuring the respective time interval includes: measuring the respective time interval between an occurrence moment of the edge of the local clock cycle during which the synchronizing signal reaches the module and the moment of the synchronizing signal reaching the module, the edge including one of a rising edge and a falling edge.

In some implementations, implementing clock synchronization between each of the plurality of modules and the calibrating module includes: acquiring at least one clock error associating the module with the calibrating module from the determined respective clock errors for the reference modules; determining a second clock error between the module and the calibrating module according to the acquired at least one clock error; and implementing the clock synchronization between the module and the calibrating module by calibrating the clock of the module with the second clock error. Calibrating the clock of the module with the second clock error can include: delaying the clock of the module with the determined second clock error.

In some examples, acquiring the at least one clock error associating the module with the calibrating module includes: obtaining, from the determined respective clock errors for the reference modules, a first reference clock error associated with the module and a particular module; obtaining a second reference clock error associated with the particular module and the calibration module; and determining the second clock error between the module and the calibrating module based on the obtained first reference clock error and second reference clock error.

In some examples, obtaining the second reference clock error associated with the particular module and the calibration module includes one of: obtaining the second reference clock error associated with the particular module and the calibration module from the determined respective clock errors for the reference modules, and obtaining, from the determined respective clock errors for the reference modules, a third reference clock error associated with the particular module and a second particular module and a fourth reference clock error associated with the second particular module and the calibration module and determining the second reference clock error based on the third reference clock error and the fourth reference clock error.

Another aspect of the present disclosure features a clock synchronizing apparatus for a clock synchronizing configuration, the apparatus including: a processor; and a non-transitory machine-readable storage medium. By invoking and executing machine-executable instructions corresponding to a clock synchronizing control logic stored on the machine-readable storage medium, the processor is caused to: select two different modules from N modules as two reference modules respectively, each of the N modules being provided a clock of a preset frequency to be synchronized, every two adjacent modules of the N modules being coupled by a transmission line of the same length, N being an odd number; control each of the reference modules to output a synchronizing signal in a way that the synchronizing signal is simultaneously transmitted in a clockwise direction and an anticlockwise direction until modules other than the reference module in the N modules respectively receive the synchronizing signal once; determine a clock error between every two modules that have the same transmission distance from the reference module according to a moment of the synchronizing signal reaching each of the other modules; select a calibrating module from the N modules; and implement clock synchronization between each of the N modules and the calibrating module according to the respective clock errors associated with each of the two reference modules.

In some examples, the clock synchronization configuration includes N−1 modules of the N modules, and the processor is caused to add an additional module to the clock synchronizing configuration to obtain the N modules, the additional module being provided with a clock of the preset frequency.

In some examples, when determining the clock error between every two modules that have the same transmission distance from the reference module according to the moment of the synchronizing signal reaching each of the other modules, the machine-executable instructions cause the processor to: for each of the other modules, measure a time interval between an edge of a local clock cycle during which the synchronizing signal reaches the module and the moment of the synchronizing signal reaching the module; and determine the clock error between every two modules that have the same transmission distance from the reference module according to the respective time intervals.

In some cases, when measuring the time interval between the edge of the local clock cycle during which the synchronizing signal reaches the module and the moment of the synchronizing signal reaching the module, the machine-executable instructions cause the processor to: measure, with a Time-to-Digital Converter (TDC), the time interval between the edge of the local clock cycle during which the synchronizing signal reaches the module and the moment of the synchronizing signal reaching the module. In some cases, when measuring the time interval between the edge of the local clock cycle during which the synchronizing signal reaches the module and the moment of the synchronizing signal reaching the module, the machine-executable instructions cause the processor to: measure, with a delay chain in Field-Programmable Gate Array (FPGA), the time interval between the edge of the local clock cycle during which the synchronizing signal reaches the module and the moment of the synchronizing signal reaching the module.

In some cases, when measuring the time interval between the edge of the local clock cycle during which the synchronizing signal reaches the module and the moment of the synchronizing signal reaching the module, the machine-executable instructions cause the processor to: measure the time interval between an occurrence moment of a rising edge of the local clock cycle during which the synchronizing signal reaches the module and the moment of the synchronizing signal reaching the module. In some cases, when measuring the time interval between the edge of the local clock cycle during which the synchronizing signal reaches the module and the moment of the synchronizing signal reaching the module, the machine-executable instructions cause the processor to: measure the time interval between an occurrence moment of a falling edge of the local clock cycle during which the synchronizing signal reaches the module and the moment of the synchronizing signal reaching the module.

When implementing clock synchronization between each of the N modules and the calibrating module according to the respective clock errors associated with each of the two reference modules, the machine-executable instructions can cause the processor to: for each of the modules, acquire at least one clock error associated with the module and the calibrating module from the respective clock errors associated with each of the two reference modules; determine a second clock error between the module and the calibrating module according to the acquired at least one clock error; and implement clock synchronization between the module and the calibrating module by calibrating the clock of the module with the second clock error. When calibrating the clock of the module with the second clock error, the machine-executable instructions can cause the processor to delay the clock of the module with the second clock error.

A further aspect of the present disclosure features a non-transitory computer-readable storage medium having instructions stored thereon which, when executed by one or more processors, cause the one or more processors to perform operations for clock synchronization, the operations including: coupling every two adjacent modules of a plurality of modules by a respective transmission line, the respective transmission lines having a same length, wherein a number of the plurality of modules is an odd number; selecting two different modules from the plurality of modules as two reference modules, respectively; obtaining, for each of the reference modules, a respective group of clock errors between every two modules in the plurality of modules; selecting a calibrating module from the plurality of modules; and implementing clock synchronization between each of the plurality of modules and the calibrating module according to the obtained respective groups of clock errors for the two reference modules.

In some implementations, obtaining the respective group of clock errors for each of the reference modules includes: controlling the reference module to transmit a respective synchronizing signal simultaneously in a clockwise direction and an anticlockwise direction via the respective transmission lines until modules other than the reference module in the plurality of modules respectively receive the synchronizing signal once; and determining, for every two modules of the other modules that have a same transmission distance from the reference module, a respective clock error between the two modules based on moments of the synchronizing signal reaching the two modules.

The details of one or more examples of the subject matter described in the present disclosure are set forth in the accompanying drawings and description below. Other features, aspects, and advantages of the subject matter will become apparent from the description, the drawings, and the claims. Features of the present disclosure are illustrated by way of example and not limited in the following figures, in which like numerals indicate like elements.

DETAILED DESCRIPTION

A PET system may include a plurality of axially arranged detector rings, and detectors on each of the detector rings may be arranged circumferentially and annularly. When photon signals are collected by the detectors in the detector ring, it is necessary to ensure synchronization of clocks between the detectors in the detector ring and thus the time for collecting data by the respective detectors in the detector ring may be consistent.

Figure 1:
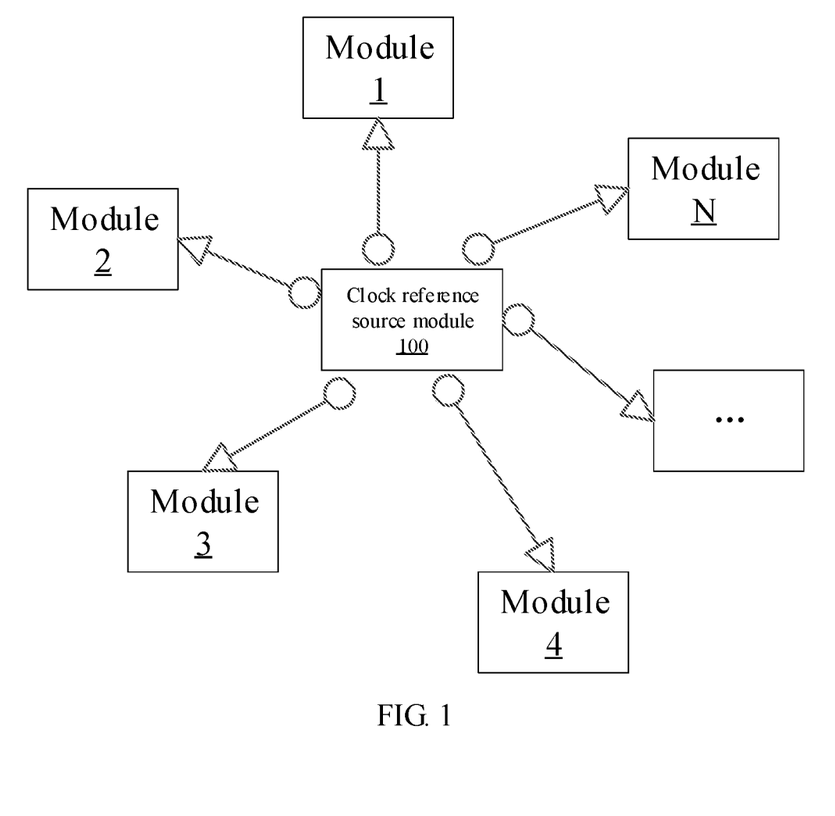
FIG. 1 is a schematic diagram of a clock synchronizing configuration according to an example of the present disclosure.

A clock synchronizing configuration may include a star configuration as shown in FIG. 1. A detector may correspond to a module to be synchronized on clock. To synchronize a clock of each module, a clock reference source 100 may be configured to provide a reference clock signal for annularly arranged N modules 1, 2, . . . , N, and then the reference clock signal may be transmitted to the respective modules 1, 2, . . . , N by N number of transmission lines of the same length. Thus, since the clock signal for the respective modules 1, 2, . . . , N is based on the same clock reference source 100 and the distance for transmitting the reference clock signal output from the clock reference source 100 to the respective modulesl, N is equal, the clock of the respective modules 1, 2, . . . , N are synchronized. However, if there is an additional clock reference source 100 provided in the above clock synchronizing configuration, design costs and structural complexity of the clock synchronizing configuration may be increased.

Implementations of the present disclosure provide a clock synchronizing method, which may be applied to a clock synchronizing configuration including N modules to be synchronized on clock. A respective clock of a preset (or predetermined) frequency may be provided in each of N modules to be synchronized on clock, and the clocks between modules may be asynchronous with each other. In an example, the clock synchronizing configuration may be a detector ring constituted by a plurality of detectors in a PET system, and each detector may include a number of crystals, a photoelectric sensor and a signal processing circuit. A detector may correspond to a module to be synchronized on clock. Besides, the clock synchronizing configuration may be another configuration to implement clock synchronization, which is not limited herein.

The number N of the modules to be synchronized on clock may be an odd number or an even number. For the two cases, modules may be connected in different manners.

Figure 2:
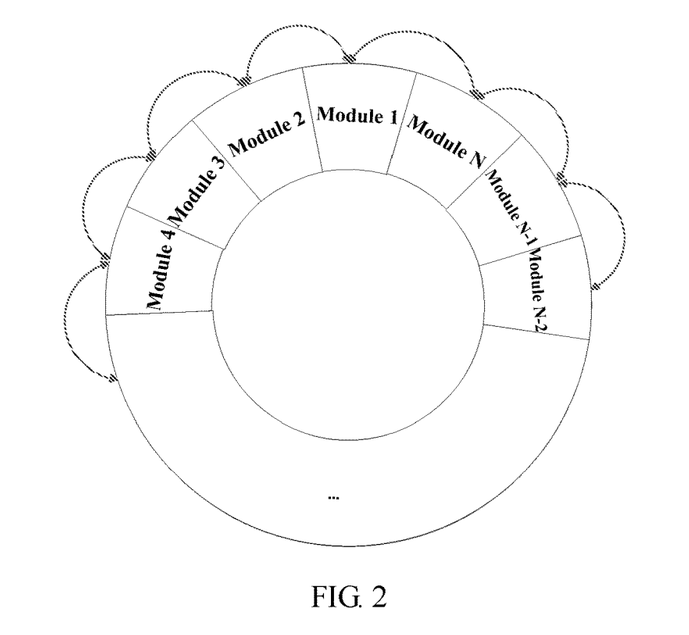
FIG. 2 is a schematic diagram of a connection manner between a plurality of modules to be synchronized on clock according to an example of the present disclosure.

FIG. 2 is a schematic diagram of a connection manner between N modules according to an example of the present disclosure. In this connection manner, the number N of the modules is an odd number, and every two adjacent modules in the N modules of the clock synchronizing configuration are coupled by a transmission line of the same length.

Figure 3:
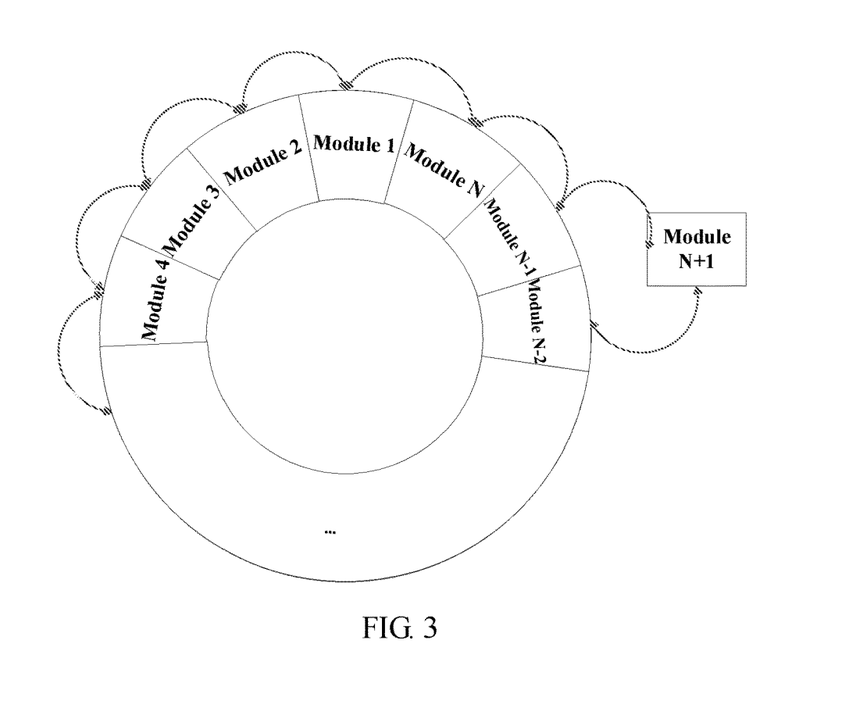
FIG. 3 is a schematic diagram of a connection manner between a plurality of modules to be synchronized on clock according to another example of the present disclosure.

FIG. 3 is a schematic diagram of a connection manner between N modules according to another example of the present disclosure. In this connection manner, the number N of the modules is an even number, an additional module to be synchronized on clock can be provided in the clock synchronizing configuration, and every two adjacent modules in the N+1 modules of the clock synchronizing configuration are coupled by the transmission line of the same length. In such a way, for any one module, the other N modules can be symmetrically arranged on left and right sides of a central line across the module. In an example, module N+1 may be added between the adjacent modules N−1, N−2 (or other two adjacent modules), and module N+1 may be coupled to module N−1 and module N−2 by two transmission lines of the same length, respectively, with module N−1 and module N−2 being not coupled. For module N+1, it can be provided with only a transmission line connection interface for clock synchronization without providing an additional interface thereon.

For example, module N+1 may be the same as other modules, or just have the same clock as other modules.

It is noted that to reduce transmission time, the length of the transmission line between every two adjacent modules may be relatively short. Besides, the respective modules in the clock synchronizing configuration may be arranged in a circular ring shape or in other shapes according to an actual application, which is not limited herein, as long as all transmission lines have the same length.

Figure 4:
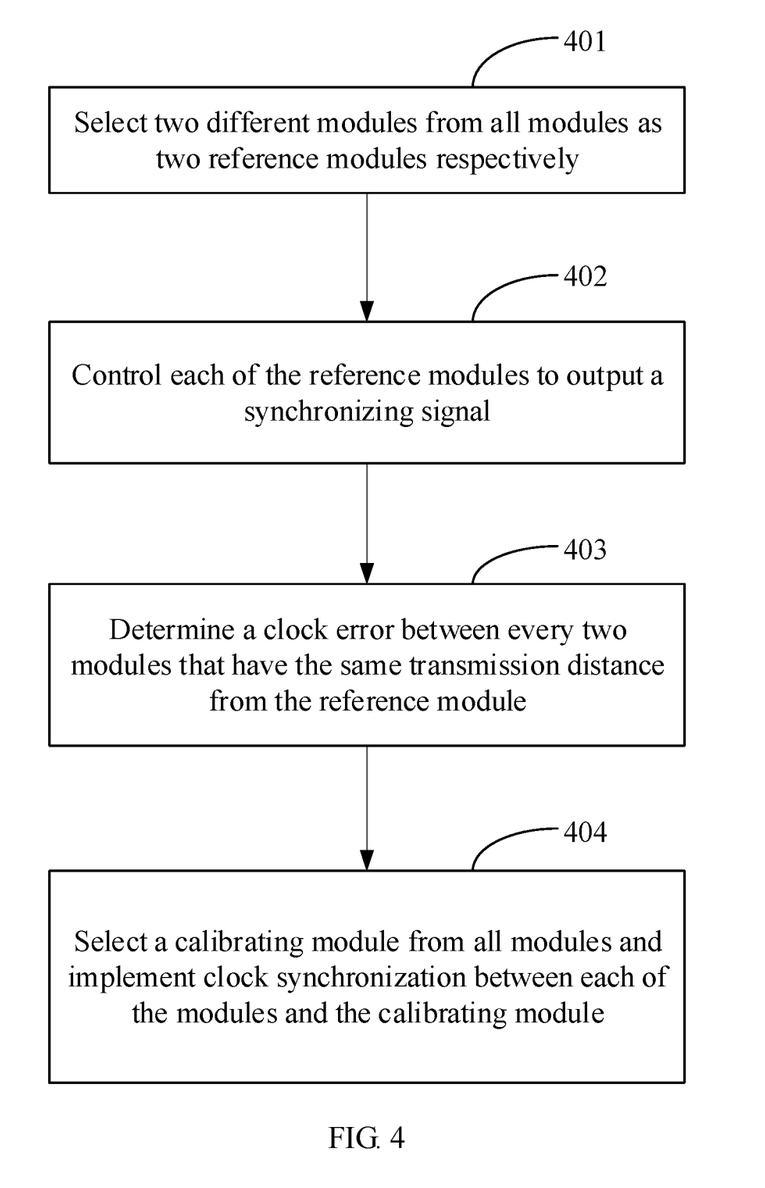
FIG. 4 is a schematic flow diagram of a clock synchronizing method according to an example of the present disclosure.

FIG. 4 is a schematic flow diagram of a process for a clock synchronizing method according to an example of the present disclosure. A clock synchronizing configuration to which the method is applied may include N number of modules. In an example, the clock synchronizing configuration may include an odd number of modules as shown in FIG. 2. In another example, the clock synchronizing configuration may include an even number of modules and an additional module as shown in FIG. 3. As shown in FIG. 4, the process may include the following steps 401-404.

At step 401, two different modules are selected from all of the modules as two reference modules, respectively.

For example, two different modules may be selected from the clock synchronizing configuration as a first reference module and a second reference module respectively. Then, the following steps 402-403 may be performed on each of the reference modules. For illustration only, steps 402-403 will be described below in detail by taking FIG. 2 as an example.

At step 402, each of the reference modules is controlled to output a synchronizing signal in a way that the synchronizing signal is simultaneously transmitted in a clockwise direction and an anticlockwise direction until modules other than the reference module respectively receive the synchronizing signal once.

For example, any module may be selected from all of the modules in the clock synchronizing configuration as the first reference module, and a circuit, e.g., a Field-Programmable Gate Array (FPGA), within the first reference module may be used to transmit a synchronizing signal SYN1 at a moment T, in a way that the synchronizing signal SYN1 is simultaneously transmitted in the clockwise direction and the anticlockwise direction through the transmission lines between the modules, until modules other than the first reference module in the clock synchronizing configuration respectively receive the synchronizing signal SYN1 once. Since the transmission line between every two adjacent modules has the same length, when the synchronizing signal SYN1 is transmitted in the clockwise direction and the anticlockwise direction for the same distance, the time used is equal in theory. For example, when the synchronizing signal SYN1 is transmitted to the modules having the same transmission distance on both right and left sides of the first reference module, the time used is equal.

Figure 5:
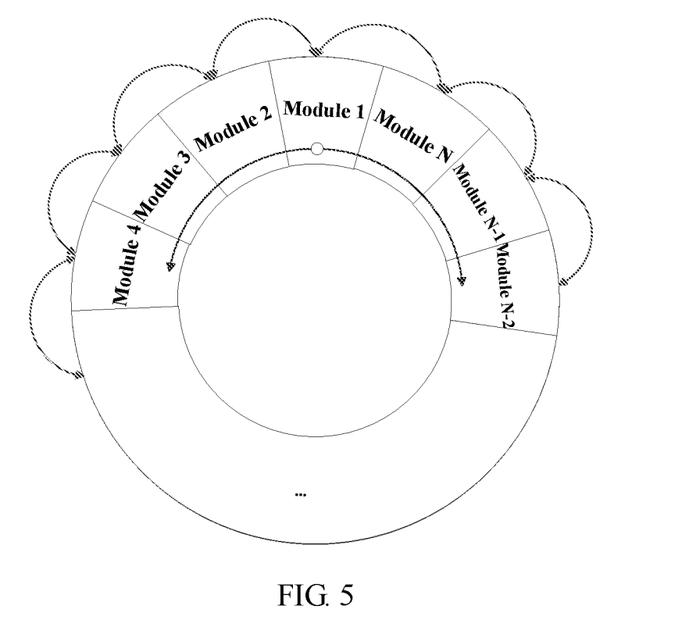
FIG. 5 is a schematic diagram of transmission of a synchronizing signal according to an example of the present disclosure.

FIG. 5 is a schematic diagram of transmission of a synchronizing signal according to an example of the present disclosure. When N is an odd number and module 1 is selected as the first reference module, the synchronizing signal SYN1 may be simultaneously transmitted in the directions indicated by two arrows in FIG. 5. During the transmission process, the synchronizing signal SYN1 is transmitted to module 2 and module N in equidistance (or equal distance), to module 3 and module N−1 in equidistance, . . . , and to module (N+1)/2 and module (N+3)/2 in equidistance. In this way, the synchronizing signal SYN1 is transmitted to module 2 and module N through equal time, to module 3 and module N−1 through equal time, . . . , and to module (N+1)/2 and module (N+3)/2 through equal time. Two modules to which the synchronizing signal SYN1 is transmitted through equal time may be paired. For example, when N=7, module 2 and module 7 are paired, module 3 and module 6 are paired, and module 4 and module 5 are paired.

Referring back to FIG. 4, at step 403, a clock error between every two modules that have the same transmission distance from the reference module, e.g., each pair of modules, is determined according to a moment of the synchronizing signal reaching each of the other modules, and thus two groups of clock errors associated with the two reference modules are obtained.

During the transmission process of the synchronizing signal SYN1, modules other than the first reference module on the clock synchronizing configuration as shown in FIG. 5 all receive the synchronizing signal SYN1 from the first reference module. Thus, two modules that have the same transmission distance from the first reference module may be taken as a pair of modules. Also, based on the moment at which the synchronizing signal SYN1 is received by each pair of modules and the operating conditions of clocks in each pair of module at the moment, a clock error between each pair of modules, e.g., a time interval between edges of the respective local clock cycle of each pair of modules, may be determined.

In one or more examples, step 403 may further includes: for each of the modules, measuring a time interval between an edge of a local clock cycle during which the synchronizing signal reaches the module and the moment of the synchronizing signal reaches the module; and for every two modules that have the same transmission distance from the reference module in the clockwise direction and the anticlockwise direction of the synchronizing signal, determining the clock error between the two modules that have the same transmission distance from the reference module according to the respective time intervals.

Figure 6:
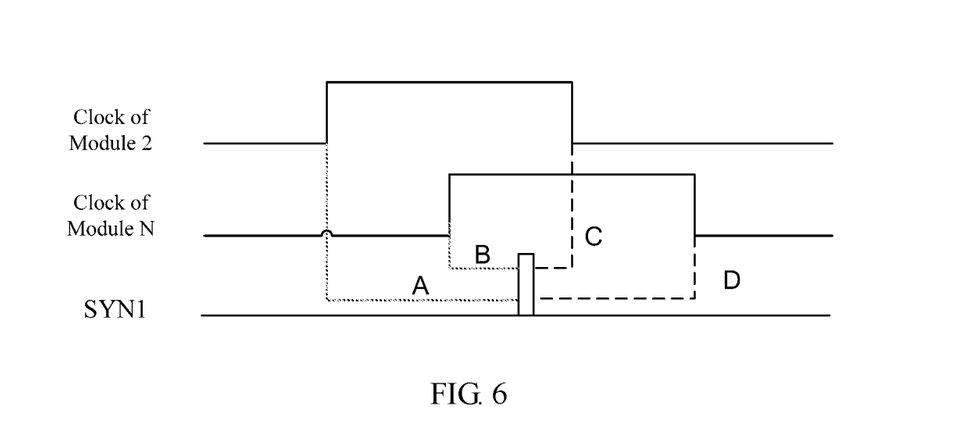
FIG. 6 is a schematic diagram of a time interval between an edge of a local clock cycle in a module and a synchronizing signal according to an example of the present disclosure.

When each pair of modules respectively receives the synchronizing signal SYN1, any module of the pair of modules may measure a time interval between an edge of a local clock cycle during which the synchronizing signal SYN1 reaches the module and the moment of the synchronizing signal SYN1 reaching the module. FIG. 6 is a schematic diagram of a clock time interval according to an example of the present disclosure. Assuming that module 1 in the clock synchronizing configuration indicated in FIG. 5 is the first reference module, for one pair of modules therein, for example, module 2 and module N, when the moment of the synchronizing signal SYN1 reaching module 2 and module N is t, module 2 may measure a time interval A between the occurrence moment of a rising edge of the local clock cycle covering moment t and moment t, and module N may also measure a time interval B between the occurrence moment of a rising edge of the local clock cycle covering moment t and moment t. Alternatively, module 2 may measure a time interval C between the occurrence moment of a falling edge of the local clock cycle covering moment t and moment t, and module N may measure a time interval D between the occurrence moment of a falling edge of the local clock cycle covering moment t and moment t.

The time interval between the edge of the local clock cycle during which the synchronizing signal is received by the module and the moment of the synchronizing signal reaching the module may be measured with a Time-to-Digital Converter (TDC) or a delay chain in FPGA in the module. For example, each of the modules may measure the time interval between the moment of the synchronizing signal SYN1 reaching the module and the edge of the local clock cycle during which the synchronizing signal is received by the module through the TDC in the module. Since the TDC can implement high precision time measuring and the time measuring accuracy is high, e.g., below 50 ps, the accuracy of the measured time interval can be effectively guaranteed. In addition, the time interval may also be measured with the delay chain in FPGA and the time measuring accuracy below 50 ps may also be implemented, thereby effectively guaranteeing the accuracy of the measured time interval.

Referring to FIG. 6, a time interval A-B may indicate a clock error between module 2 and module N. For example, the time interval A-B may indicate the local clock of module 2 is earlier than the local clock of module N by a length of time A-B. Alternatively, a time interval C-D may also indicate a clock error between module 2 and module N. For example, the time interval C-D may indicate the local clock of module 2 is earlier than the local clock of module N by a length of time C-D. In some cases, the local clocks of module 2 and module N have the same period, and the length of time A-B is identical to the length of time C-D. In some cases, the local clocks of module 2 and module N have different periods, and the length of time A-B is different from the length of time C-D.

Figure 7:
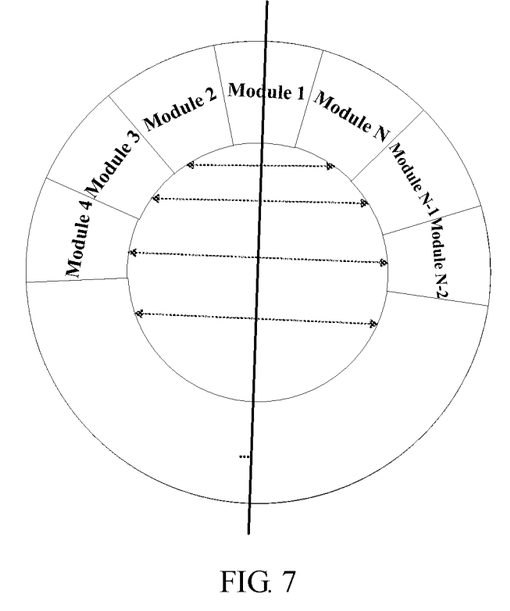
FIG. 7 is a schematic diagram of modules in pairs according to an example of the present disclosure.

When a diameter at which the first reference module is located is taken as a symmetry axis, the clock error between each pair of modules may be measured with the above method. FIG. 7 is a diagram of modules in pairs according to an example of the present disclosure. When module 1 is taken as the first reference module, the clock error between each pair of modules may be measured and stored.

Figure 8:
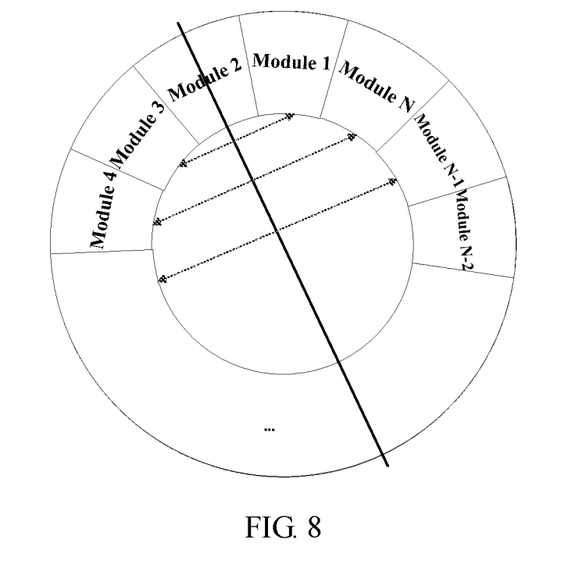
FIG. 8 is a schematic diagram of modules in pairs according to another example of the present disclosure.

Next, another one module may be selected from all modules as a second reference module. The second reference module is different from the above first reference module. Then, with the same manner as described above, the second reference module is controlled to produce a synchronizing signal SYN2. With the same transmission manner and measuring manner as described above, when a diameter at which the second reference module is located as a symmetry axis, the clock error between each pair of modules may be obtained. For example, assuming module 2 is selected as the second reference module, the diagram of modules in pairs as shown in FIG. 8 can be obtained by repeating the above process and the clock error between each pair of modules may be measured and stored.

It is noted that in examples of the present disclosure, two groups of clock errors associated with two reference modules may be respectively or simultaneously obtained with the above manner.

Two groups of clock errors respectively associated with the first reference module and the second reference module can be obtained. For example, when the total number of the modules is 7 and module 1 and module 2 are respectively taken as the first reference module and the second reference module, the clock error between each pair of modules indicated in Table 1 may be obtained respectively.

TABLE 1

| Clock errors between pairs of modules | |
|---|---|
| Module 1 as the first reference module | Module 2 as the second reference module |
| Clock error 1 between module 2 and module 7 | Clock error 4 between module 3 and module 1 |
| Clock error 2 between module 3 and module 6 | Clock error 5 between module 4 and module 7 |
| Clock error 3 between module 4 and module 5 | Clock error 6 between module 5 and module 6 |

Figure 9:
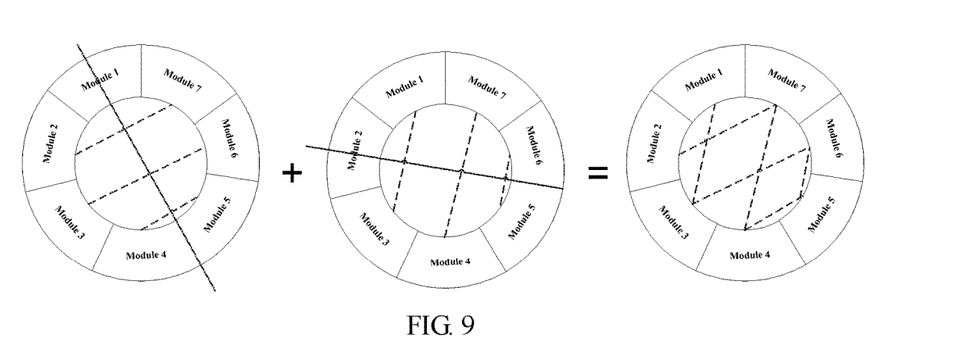
FIG. 9 is a schematic diagram of a clock error relationship between modules according to an example of the present disclosure.

FIG. 9 is a schematic diagram of a clock error relationship between modules according to an example of the present disclosure. The clock error relationship between all modules may be obtained according to the clock error between each pair of modules in Table 1 as shown in FIG. 9.

Referring back to FIG. 4, at step 404, a calibrating module is selected from all of the modules and clock synchronization between each of the modules and the calibrating module may be implemented according to the respective clock errors associated with each of the two reference modules.

In one or more examples, step 404 may further include: for each of the modules, acquiring at least one clock error that associates the module with the calibrating module from the obtained two groups of clock errors; determining a second clock error between the module and the calibrating module according to the acquired at least one clock error; and implementing clock synchronization between the module and the calibrating module by calibrating the module with the second clock error.

In this example, any module may be selected as a calibrating module from all of the modules. The clock of the calibrating module is the calibrating clock. For each of the modules, at least one clock error associated the module with the calibrating module may be acquired in above Table 1. A second clock error between the clock of the module and the calibrating clock may be determined according to the acquired at least one clock error.

In some cases, a module and the calibration module are directly associated with a clock error in the obtained two groups of clock errors, and the second clock error between the clock of the module and the calibrating clock can be acquired based on the clock error, e.g., the second clock error can be identical to the clock error. In some cases, In some cases, a module and the calibration module are indirectly associated via one or more other modules, and the second clock error between the module and the calibration module can be determined based on respective associated clock errors in the obtained two groups of the clock errors. For example, the module and the calibration module are not directly associated with any clock error in the obtained two groups of clock errors. Instead, the module and a first module are associated with clock error A in the obtained two groups of the clock errors, and the calibration module and the first module are associated with clock error B in the obtained two groups of the clock errors. Thus, the second clock error between the module and the calibration module can be determined based on clock error A and clock error B, e.g., the second clock error can be identical to a sum of clock error A and clock error B.

As noted above, module 1 is taken as the calibrating module, and then the second clock error between the clock of each of the modules 3, 6, 5, 4, 7, 2 and the calibrating clock may be obtained sequentially through Table 1. In an example, referring to Table 1 and FIG. 9, clock error D1 between the clock of module 3 and the calibrating clock is acquired based on clock error 4, clock error D2 between the clock of module 6 and the calibrating clock is acquired based on clock error D1 and clock error 2, clock error D3 between the clock of module 5 and the calibrating clock is acquired based on clock error D2 and clock error 6, clock error D4 between the clock of module 4 and the calibrating clock is acquired based on clock error D3 and clock error 3, clock error D5 between the clock of module 7 and the calibrating clock may be acquired based on clock error D4 and clock error 5, and clock error D6 between the clock of module 2 and the calibrating clock may be acquired based on clock error D5 and clock error 1.

Figure 10:
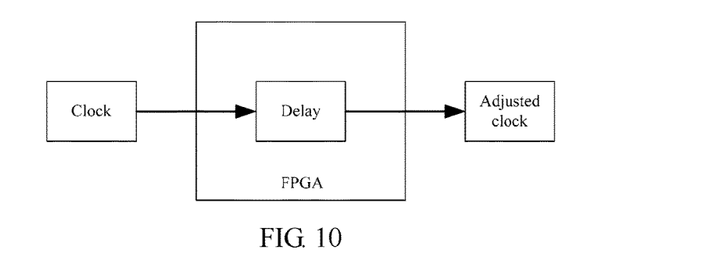
FIG. 10 is a schematic diagram of clock delay calibration according to an example of the present disclosure.

After obtaining the second clock error between the clock of each module (excluding calibrating module) and the calibrating clock, the clock of each module may be calibrated according to the corresponding second clock error with a calibration manner. FIG. 10 is a schematic diagram of clock delay calibration for an example calibration manner. For example, for each of the modules, the clock of the module may be delayed with the corresponding second clock error by using FPGA in the module, so that the delayed clock (may be also referred to as an adjusted clock as shown in FIG. 10) of the module is synchronized with the calibrating clock. In this way, clock synchronization between each of the modules and the calibrating module can be implemented.

According to the method in the present disclosure, every two adjacent modules of all 2M+1 modules in a configuration or all 2M modules and an additional module in the clock synchronizing configuration may be coupled with a transmission line of the same length. M is an integer greater than zero. When performing clock synchronization, two different modules are selected from all modules as two reference modules. Each of the reference modules is controlled to output a synchronizing signal in a way that the synchronizing signal is simultaneously transmitted in a clockwise direction and an anticlockwise direction until modules other than the reference module in the N modules respectively receive the synchronizing signal once. A clock error between every two modules that have the same transmission distance from the reference module is determined according to a moment of the synchronizing signal reaching each of the other modules. A calibrating module is selected from the N modules. Clock synchronization between each of the N modules and the calibrating module is implemented according to the respective clock errors associated with each of the two reference modules. In some cases, three or more modules may be selected from all of the modules as reference modules, and accordingly three or more groups of clock errors can be obtained. The clock synchronization between the modules can be achieved based on the obtained three or more groups of clock errors. The technical solution of the present disclosure can effectively reduce design costs and structural complexity of the clock synchronizing configuration.

Figure 11:
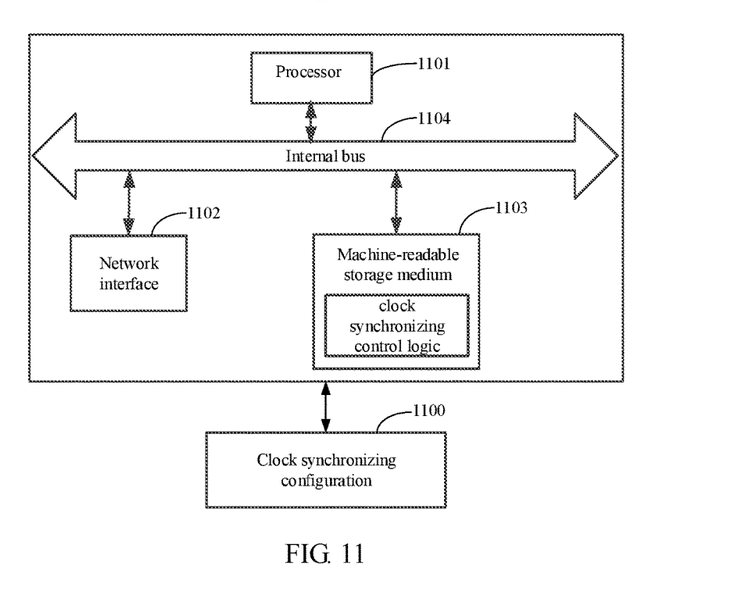
FIG. 11 is a schematic diagram of a hardware structure of a clock synchronizing apparatus according to an example of the present disclosure.

FIG. 11 is a schematic diagram of a hardware structure of a clock synchronizing apparatus according to an example of the present disclosure. The clock synchronizing apparatus may be applied a clock synchronizing configuration 1100. The clock synchronizing configuration 1100 includes a respective clock of a preset frequency provided in each of N modules to be synchronized on clock, and every two adjacent modules of the N modules coupled by a transmission line of the same length when N is an odd number. The clock synchronizing configuration 1100 may be as shown in FIGS. 2-3, which will not be detailed herein. The clock synchronizing apparatus may be implemented by software, hardware or a combination thereof. From a level of hardware, in addition to a processor 1101, a network interface 1102, machine-readable storage medium 1103 and an internal bus 1104, the clock synchronizing apparatus may further include other hardware according to actual functions, and further detail is omitted for brevity.

In different examples, the machine-readable storage medium 1103 may be a Read-Only Memory (ROM), a volatile memory, a non-volatile memory, a flash memory, a storage drive (e.g. hard disk drive), a solid state hard disk, any type of storage disk (e.g., optical disk, Digital Video Disk (DVD)), or a similar storage medium, or a combination thereof.

Figure 12:
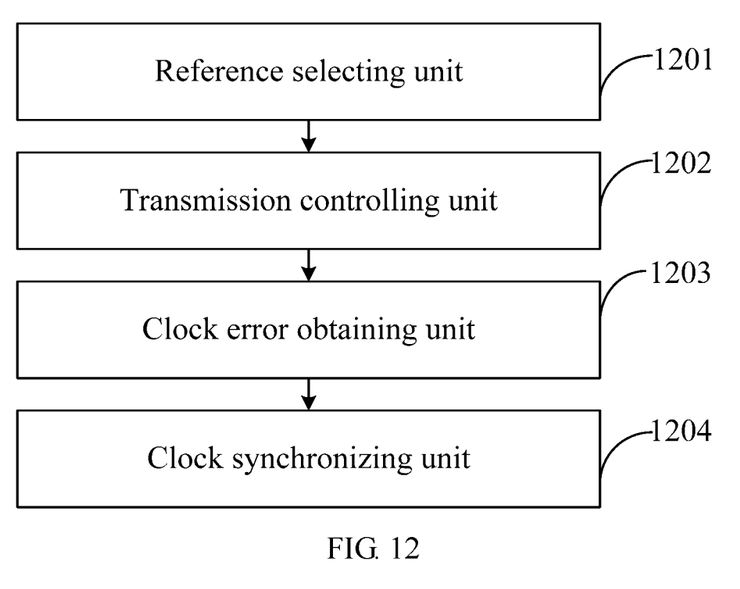
FIG. 12 is a schematic diagram of function modules of clock synchronizing logic according to an example of the present disclosure.

Further, the machine-readable storage medium 1103 stores machine-executable instructions corresponding to clock synchronizing control logic. As shown in FIG. 12, functionally, the control logic may include: a reference selecting unit 1201, a transmission controlling unit 1202, a clock error obtaining unit 1203, and a clock synchronizing unit 1204.

The reference selecting unit 1201 is configured to select two different modules from the N modules as two reference modules respectively.

The transmission controlling unit 1202 is configured to control each of the reference modules to output a synchronizing signal in a way that the synchronizing signal is simultaneously transmitted in a clockwise direction and an anticlockwise direction until other modules than the reference module in the N modules respectively receive the synchronizing signal once.

The clock error obtaining unit 1203 is configured to determine a clock error between every two modules that have the same transmission distance from the reference module according to a moment of the synchronizing signal reaching each of the other modules.

The clock synchronizing unit 1204 is configured to select a calibrating module from the N modules and implement clock synchronization between each of the N modules and the calibrating module according to the respective clock errors associated with each of the two reference modules.

In one or more examples, when N is an even number, an additional module to be synchronized is added in the clock synchronizing configuration. The additional module is provided with a clock of the preset frequency, and every two adjacent modules of the N+1 modules are coupled by the transmission line of the same length.

In one or more examples, the clock error obtaining unit 1103 may include an interval measuring subunit and a clock error obtaining subunit.

The interval measuring subunit is configured to, for each of the other modules, measure a time interval between an edge of a local clock cycle during which the synchronizing signal reaches the module and the moment of the synchronizing signal reaching the module.

The clock error obtaining subunit is configured to determine the clock error between every two modules that have the same transmission distance from the reference module according to the respective time intervals.

Where, the interval measuring subunit may be configured to measure the time interval between the edge of the local clock cycle during which the synchronizing signal reaches the module and the moment of the synchronizing signal reaching the module with a Time-to-Digital Converter (TDC) or a delay chain in Field Programmable Gate Array (FPGA).

In some examples, the clock synchronizing unit may be further configured to, for each of the modules, acquire at least one clock error associated the module with the calibrating module from the respective clock errors associated with each of the two reference modules; determine a second clock error between the module and the calibrating module according to the acquired at least one clock error; and implement clock synchronization between the module and the calibrating module by calibrating the clock of the module with the second clock error. In an example, calibrating the clock of the module with the second clock error comprises delaying the clock of the module with the second clock error.

Taking the software implementation as an example, it is further described that how the clock synchronizing apparatus runs the clock synchronizing control logic. In this example, the clock synchronizing control logic of the present disclosure should be understood as machine-executable instructions stored in the machine-readable storage medium 1103. When the processor 1101 on the clock synchronizing apparatus of the present disclosure executes the clock synchronizing control logic, the processor 1101 may be caused to execute the above clock synchronizing method by invoking the machine-executable instructions corresponding to the clock synchronizing control logic stored on the machine-readable storage medium 1103.

For simplicity and illustrative purposes, the present disclosure is described by referring mainly to examples thereof. In the above descriptions, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure. As used herein, the terms "a" and "an" are intended to denote at least one of a particular element, the term "includes" means includes but not limited to, the term "including" means including but not limited to, and the term "based on" means based at least in part on.

The above description merely provides examples of the present disclosure and is not intended to limit the present disclosure in any form. Although the present disclosure is disclosed by the above examples, the examples are not intended to limit the present disclosure. Those skilled in the art, without departing from the scope of the technical scheme of the present disclosure, may make a plurality of changes and modifications of the technical scheme of the present disclosure by the method and technical content disclosed above.

Therefore, without departing from the scope of the technical scheme of the present disclosure, based on technical essences of the present disclosure, any simple alterations, equal changes and modifications should fall within the protection scope of the technical scheme of the present disclosure. Accordingly, other examples are within the scope of the following claims.

The invention claimed is:

1. A clock synchronizing method comprising:
    coupling every two adjacent modules of a plurality of modules by a respective transmission line, the respective transmission lines having a same length, each module having a respective clock of a preset frequency to be synchronized, wherein a number of the plurality of modules N is an odd number;
    selecting two different modules from the plurality of modules as two reference modules, respectively;
    for each of the reference modules,
        controlling the reference module to transmit a respective synchronizing signal simultaneously in a clockwise direction and an anticlockwise direction via the respective transmission lines until modules other than the reference module in the plurality of modules respectively receive the synchronizing signal once;
        determining, for every two modules of the other modules that have a same transmission distance from the reference module, a respective clock error between the two modules based on moments of the synchronizing signal reaching the two modules;
    selecting a calibrating module from the plurality of modules; and
    implementing clock synchronization between each of the plurality of modules and the calibrating module according to the determined respective clock errors for the two reference modules by
        acquiring at least one clock error associating the module with the calibrating module from the determined respective clock errors for the reference modules,
        determining a second clock error between the module and the calibrating module according to the acquired at least one clock error, and
        implementing the clock synchronization between the module and the calibrating module by calibrating the clock of the module with the second clock error.

2. The method of claim 1, wherein a clock synchronization configuration comprises N−1 modules of the plurality of modules, and
    wherein the method further comprises:
        adding an additional module to the N−1 modules to obtain the N modules, the additional module being provided with a clock of the preset frequency to be synchronized.

3. The method of claim 1, wherein determining the respective clock error between the two modules based on moments of the synchronizing signal reaching the two modules comprises:
    for each of the two modules, measuring a respective time interval between an edge of a local clock cycle during which the synchronizing signal reaches the module and the moment of the synchronizing signal reaching the module; and
    determining the clock error between the two modules based on the measured respective time intervals.

4. The method of claim 3, wherein measuring the respective time interval comprises:
    using at least one of a Time-to-Digital Converter (TDC) or a delay chain in Field-Programmable Gate Array (FPGA) in the module.

5. The method of claim 3, wherein measuring the respective time interval comprises:
    measuring the respective time interval between an occurrence moment of the edge of the local clock cycle during which the synchronizing signal reaches the module and the moment of the synchronizing signal reaching the module, the edge comprising one of a rising edge and a falling edge.

6. The method of claim 1, wherein calibrating the clock of the module with the second clock error comprises:
    delaying the clock of the module with the determined second clock error.

7. The method of claim 1, wherein acquiring the at least one clock error associating the module with the calibrating module comprises:
    obtaining, from the determined respective clock errors for the reference modules, a first reference clock error associated with the module and a particular module;
    obtaining a second reference clock error associated with the particular module and the calibration module; and
    determining the second clock error between the module and the calibrating module based on the obtained first reference clock error and second reference clock error.

8. The method of claim 7, wherein obtaining the second reference clock error associated with the particular module and the calibration module comprises one of:
    obtaining the second reference clock error associated with the particular module and the calibration module from the determined respective clock errors for the reference modules, and
    obtaining, from the determined respective clock errors for the reference modules, a third reference clock error associated with the particular module and a second particular module and a fourth reference clock error associated with the second particular module and the calibration module and determining the second reference clock error based on the third reference clock error and the fourth reference clock error.

9. A clock synchronizing apparatus for a clock synchronizing configuration, the apparatus comprising:

a processor; and a non-transitory machine-readable storage medium, wherein, by invoking and executing machine-executable instructions corresponding to a clock synchronizing control logic stored on the machine-readable storage medium, the processor is caused to:

select two different modules from N modules as two reference modules respectively, each of the N modules being provided a clock of a preset frequency to be synchronized, every two adjacent modules of the N modules being coupled by a transmission line of the same length, N being an odd number;

control each of the reference modules to output a synchronizing signal in a way that the synchronizing signal is simultaneously transmitted in a clockwise direction and an anticlockwise direction until modules other than the reference module in the N modules respectively receive the synchronizing signal once;

determine a clock error between every two modules that have the same transmission distance from the reference module according to a moment of the synchronizing signal reaching each of the other modules;

select a calibrating module from the N modules; and implement clock synchronization between each of the N modules and the calibrating module according to the respective clock errors associated with each of the two reference modules by acquiring at least one clock error associating the module with the calibrating module from the determined respective clock errors for the reference modules, determining a second clock error between the module and the calibrating module according to the acquired at least one clock error, and implementing the clock synchronization between the module and the calibrating module by calibrating the clock of the module with the second clock error.

10. The apparatus of claim 9, wherein the clock synchronization configuration comprises N−1 modules of the N modules, and wherein the processor is caused to add an additional module to the clock synchronizing configuration to obtain the N modules, the additional module being provided with a clock of the preset frequency.

11. The apparatus of claim 9, wherein, when determining the clock error between every two modules that have the same transmission distance from the reference module according to the moment of the synchronizing signal reaching each of the other modules, the machine-executable instructions cause the processor to:

for each of the other modules, measure a time interval between an edge of a local clock cycle during which the synchronizing signal reaches the module and the moment of the synchronizing signal reaching the module; and determine the clock error between every two modules that have the same transmission distance from the reference module according to the respective time intervals.

12. The apparatus of claim 11, wherein, when measuring the time interval between the edge of the local clock cycle during which the synchronizing signal reaches the module and the moment of the synchronizing signal reaching the module, the machine-executable instructions cause the processor to:

measure, with a Time-to-Digital Converter (TDC), the time interval between the edge of the local clock cycle during which the synchronizing signal reaches the module and the moment of the synchronizing signal reaching the module.

13. The apparatus of claim 11, wherein, when measuring the time interval between the edge of the local clock cycle during which the synchronizing signal reaches the module and the moment of the synchronizing signal reaching the module, the machine-executable instructions cause the processor to:

measure, with a delay chain in Field-Programmable Gate Array (FPGA), the time interval between the edge of the local clock cycle during which the synchronizing signal reaches the module and the moment of the synchronizing signal reaching the module.

14. The apparatus of claim 11, wherein, when measuring the time interval between the edge of the local clock cycle during which the synchronizing signal reaches the module and the moment of the synchronizing signal reaching the module, the machine-executable instructions cause the processor to:

measure the time interval between an occurrence moment of a rising edge of the local clock cycle during which the synchronizing signal reaches the module and the moment of the synchronizing signal reaching the module.

15. The apparatus of claim 11, wherein, when measuring the time interval between the edge of the local clock cycle during which the synchronizing signal reaches the module and the moment of the synchronizing signal reaching the module, the machine-executable instructions cause the processor to:

measure the time interval between an occurrence moment of a falling edge of the local clock cycle during which the synchronizing signal reaches the module and the moment of the synchronizing signal reaching the module.

16. The apparatus of claim 9, wherein, when calibrating the clock of the module with the second clock error, the machine-executable instructions cause the processor to:

delay the clock of the module with the second clock error.

17. A non-transitory computer-readable storage medium having instructions stored thereon which, when executed by one or more processors, cause the one or more processors to perform operations for clock synchronization, the operations comprising:

coupling every two adjacent modules of a plurality of modules by a respective transmission line, the respective transmission lines having a same length, wherein a number of the plurality of modules is an odd number;

selecting two different modules from the plurality of modules as two reference modules, respectively;

obtaining, for each of the reference modules, a respective group of clock errors between every two modules in the plurality of modules;

selecting a calibrating module from the plurality of modules; and implementing clock synchronization between each of the plurality of modules and the calibrating module according to the obtained respective groups of clock errors for the two reference modules by acquiring at least one clock error associating the module with the calibrating module from the determined respective clock errors for the reference modules, determining a second clock error between the module and the calibrating module according to the acquired at least one clock error, and implementing the clock synchronization between the module and the calibrating module by calibrating the clock of the module with the second clock error.

18. The non-transitory computer-readable storage medium of claim 17, wherein obtaining the respective group of clock errors for each of the reference modules comprises:

controlling the reference module to transmit a respective synchronizing signal simultaneously in a clockwise direction and an anticlockwise direction via the respective transmission lines until modules other than the reference module in the plurality of modules respectively receive the synchronizing signal once; and determining, for every two modules of the other modules that have a same transmission distance from the reference module, a respective clock error between the two modules based on moments of the synchronizing signal reaching the two modules.

* * * * *